US00PP18729P3

(12) United States Plant Patent
Olesen

(10) Patent No.: US PP18,729 P3
(45) Date of Patent: Apr. 15, 2008

(54) MINIATURE ROSE PLANT NAME 'POULPAH024'

(50) Latin Name: ***Rosa* hybrid**
Varietal Denomination: Poulpah024

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 119 days.

(21) Appl. No.: 11/298,193

(22) Filed: Dec. 9, 2005

(65) Prior Publication Data

US 2007/0136903 P1 Jun. 14, 2007

(51) Int. Cl.
*A01H 5/00* (2006.01)

(52) U.S. Cl. ..... Plt./116

(58) Field of Classification Search ..... Plt./116, Plt./123, 141, 143
See application file for complete search history.

*Primary Examiner*—Howard J. Locker

(57) ABSTRACT

A new rose plant that has abundant, red, white, and yellow flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpah024'.

SUMMARY OF THE INVENTION

The present invention constitutes a new and distinct variety of rose plant which originated from a controlled crossing between the female seed parent, an unnamed seedling, and the male pollen parent, 'Poulra020', a non-patented variety from the same inventor. The two parents were crossed in 2001 and the resulting seeds were planted in a controlled environment. The new variety is named 'Poulpah024'.

The new rose may be distinguished from its seed parent by the following combination of characteristics:

1. 'Poulpah024' normally has 90 flower petals, 10 to 15 of which are petaloids. The female parent has about 50 petals.
2. Flowers of 'Poulpah024' are red, blended with yellow and white stripes. The female parent has light pink flowers.
3. 'Poulpah024' flower bloom diameter is 55 to 60 mm. The female parent has a flower bloom diameter of 35 to 40 mm.

The new variety may be distinguished from the pollen parent 'Poulra020' by the following combination of characteristics:

1. 'Poulpah024' normally has 90 flower petals, 10 to 15 of which are petaloids. 'Poulra020' has approximately 25 to 35 petals.
2. 'Poulpah024' has an ovate bud form while the pollen parent has an ovoid to globular bud form.

The objective of the hybridization of this rose variety for commercial culture was to create a new and distinct variety with unique qualities, such as:

1. Uniform and abundant red, yellow, and white flowers;
2. Vigorous and compact growth;
3. Year-round flowering under glasshouse conditions;

4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah024' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpah024' was selected by the inventor as a single plant from the progeny of the hybridization in June 2002.

Asexual reproduction of 'Poulpah024' by vegetative cuttings and traditional budding was first done by Mogens N. Olesen in the nursery in Fredensborg, Denmark in April 2002. This initial and other subsequent propagations conducted in controlled environments have demonstrated that the characteristics of 'Poulpah024' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah024'. Specifically illustrated in the drawing:

FIG. 1.1; Flower buds at various stages of opening;

FIG. 1.2; Open flower and flower petals detached;

FIG. 1.3; Sepals, receptacle, and pedicel;

FIG. 1.4; Juvenile growth;

FIG. 1.5; Bare stem;

FIG. 1.6; Mature leaves.

DETAILED DESCRIPTION OF THE VARIETY

The following is a description of 'Poulpah024', as observed in its growth in glasshouses in Odense, Denmark. Observed plants are 4 months of age. Color references are made using The Royal Horticultural Society (London, England) Colour Chart, 2001, except where common terms of color are used.

For a comparison, several physical characteristics of the rose variety 'POULcub', a rose variety from the same inventor described and illustrated in U.S. Plant patent application Ser. No. 10/647,010 dated Aug. 21, 2003, now abandoned, are compared to 'Poulpah024' in Chart 1.

CHART 1

| | 'Poulpah024' | 'Poulcub' |
|---|---|---|
| Petalage. | 90 petals under normal conditions, 10 to 15 of which are petaloids. | Average range: 15 to 17 petals under normal conditions with 20 petaloids. |
| Upper surface of petal on open flower. | Red-Purple Group 57A to 58B with streaks of White Group 155B or Yellow Group 5D. Occasionally the foreground and background colors are reversed. | Red-Purple Group 66A, Yellow Group 2B, White Group 155A. |
| Flower diameter. | Average flower diameter is 55 to 60 mm when open. | Average flower diameter is 35 to 40 mm when open. |

FLOWER AND FLOWER BUD

Blooming habit: Continuous.

Flower bud:

*Size.*—As sepals begin to separate, flower buds are normally 20 mm in length from base of receptacle to the apex. Normally 11 mm in diameter.

*Bud form.*—Ovate.

*Bud color.*—As sepals unfold the petals are Red-Purple Group 57A and Yellow Group 8B in color.

*Sepals.*—Upper Surface: The basal one-third of the sepal is Yellow-Green Group 147A. Base is Yellow-Green Group 145A. Light pubescence observed. Lower Surface: Yellow-Green Group 146A. Anthocyanic pigments the color of Greyed-Orange 173A observed at the apex. Smooth in texture. Shape: The apex is normally cirrose. On occasion, sepals broaden towards the apex. The base is flat at the union with the receptacle. Margins: Margins have strong foliaceous appendages, which are occasionally lined with stipitate glands. Size: Normally 30 to 50 mm (l) by 9 mm (w).

*Receptacle.*—Texture: Smooth. Shape: Funnel shaped to urn shaped. Size: 5 mm (h)×7 mm (w). Color: Yellow-Green Group 144B.

*Peduncle.*—Surface: Somewhat rough with few stipitate glands. Length: 35 to 40 mm. Diameter: 3 mm. Color: Yellow-Green Group 144A. Strength: Strong.

*Borne.*—Singularly and in clusters of 3 flower buds per stem.

Flower bloom:

*Fragrance.*—Light floral to medium rose scent.

*Duration.*—As a pot plant, flowers last up to 18 days. Petals do not fall cleanly away from plant after flowers have fully matured.

*Size.*—Flower diameter is normally 55 to 60 mm when open. Average depth is 25 mm.

*Form.*—Rosette with many overlapping petals of different sizes.

*Shape of flower when viewed from the side.*—Upon opening, upper part: Flattened convex. Upon opening, lower part: Flat. Open flower, upper part: Flattened convex. Open flower, lower part: Concave.

*Petalage.*—On average, flowers exhibit 90 petals, 10 to 15 of which are petaloids.

Flower color:

*Upon opening, petals.*—Outermost petals: Upper Surface: Steaks of Red-Purple 58B and Red Group 42A at the middle zone layered over yellow coloration which is Yellow Group 8D at the apex and Yellow Group 4B at middle zone. Lower Surface: Streaks of Red-Purple Group 58B and 58C and Yellow Group 8D at apex. Yellow Group 4B at middle and basal zone. Innermost petals: Upper Surface: Steaks of Red-Purple 58B and Red Group 42A at the middle zone layered over yellow coloration which is Yellow Group 8D at the apex and Yellow Group 4B at middle zone. Lower Surface: Streaks of Red-Purple Group 58B and 58C and Yellow Group 8D at apex. Yellow Group 4B at middle and basal zone.

*Upon opening, basal petal spots.*—Upper Surface: Yellow Group 5A. Lower Surface: None.

*After opening, petals.*—Outermost petals: Upper Surface: Red-Purple Group 57A to 58B with streaks of White Group 155B and or Yellow Group 5D layered over. Occasionally the red-purple colors appear as being layered over the yellow and white. Lower Surface: Red-Purple Group 64D with streaks of White Group 155B and or Yellow Group 5D layered over. Occasionally the red-purple colors appear as being layered over the yellow and white. Innermost petals: Upper Surface: Red-Purple Group 57A to 58B at apex, blending to Red Group 42A at the middle zone. Streaks of White Group 155B and or Yellow Group 5D and 5B are layered over. Occasionally the red and red-purple colors appear as being layered over the yellow and white. Lower Surface: Red-Purple Group 64D with streaks of White Group 155B and Yellow Group 5D layered over. Occasionally the red and red-purple colors appear as being layered over the yellow and white.

*After opening, basal petal spots.*—Outermost petals: Upper Surface: Yellow Group 4A. Lower Surface: Yellow Group 4B.

General tonality: On open flower Red-Purple Group 57A with streaks of White Group 155A and Yellow Group 5D. No change in tonality at the end of the $18^{th}$ day.

Petals:

*Petal reflex.*—Weak.

*Petal margin.*—Entire and uniform. Week undulations of margin observed.

*Shape.*—Narrow elliptical. Base: Acute. Apex: Cuspidate.

*Size.*—22 to 30 mm (l)×15 to 30 mm (w).

*Texture.*—Smooth.

*Thickness.*—Average.

*Arrangement.*—Not formal.

Petaloids:

*Quantity.*—10 to 15 normally.

*Size.*—12 mm (l)×9 mm (w).

*Shape.*—Narrow elliptical to irregular.

*Color.*—

*Upper surface.*—Yellow Group 9B with streaks of Red Group 42A.

*Lower surface.*—Yellow Group 9C with streaks of Red Group 42B.

Reproductive organs:

*Pollen.*—None observed.

*Anthers.*—Size: 2 mm long. Color: Yellow Group 6D with Yellow-Orange Group 14A towards margins. Quantity: 65 to 75.

*Filaments.*—Color: Yellow Group 7B. Length: 4 to 5 mm.

*Pistils.*—Length: 8 to 9 mm. Quantity: Average 35 to 45.

*Stigmas.*—Superior relative to the length of the filaments and the height of the anthers. Color: Yellow-Green Group 150B.

*Styles.*—Color: Yellow-Green Group 150D.

*Seed formation.*—Not observed.

PLANT

Plant growth: Moderate, upright to bushy. When grown as a 12 cm pot plant on its own roots, the average height of the plant itself is 20 to 25 cm and the average width is 15 to 20 cm.

Stems:

*Color.*—Young wood: Yellow-Green Group 144B. Older wood: Yellow-Green Group 146C. Diameter: 2 mm. Internodal distance: 30 mm. Length of stems: On average canes are 20 cm from the base of the stem to the flowering portion. Surface Texture: Young wood: Smooth. Older wood: Smooth.

Prickles:

*Incidence.*—3 prickles per 10 cm of stem on average.

*Color.*—Juvenile thorns are Greyed-Yellow Group 160D. Mature prickles are Greyed-Red Group 181C.

*Shape.*—Upper side is flat. Lower side is concave.

Plant foliage: Normal number of leaflets on normal leaves in middle of the stem: 5 leaflets.

*Compound leaf size.*—90 to 95 mm (l)×70 to 75 mm (w).

*Quantity.*—3 leaves per 10 cm of stem.

*Foliage color.*—Mature foliage is Yellow-Green Group 147A on the upper surface. Lower surface is Yellow-Green Group 147B. Juvenile foliage, on the upper surface, is Yellow-Green Group 144A with marginal anthocyanic intonations of Greyed-Red Group 181A. Lower surface is Yellow-Green Group 144B.

Plant leaves and leaflets:

*Stipules.*—Size: 10 mm in length. Shape: Linear, slightly broad based with outward extending apices. Margins: Finely serrated with many stipitate glands. Color: Yellow-Green 147A.

*Petiole.*—Length: 10 to 15 mm. Diameter: 1.5 mm. Color: Upper surface is Yellow-Green Group 144A. Lower surface is Yellow-Green Group 144A. Underneath: Smooth with few stipitate glands observed.

*Rachis.*—Size: 30 mm in length. Color: Upper surface is Yellow-Green Group 144A. Lower surface is Yellow-Green Group 145A. Underneath: Few small prickles and stipitate glands observed.

*Leaflet.*—Average Size: 45 mm (l)×30 mm (w). Margin: Serrate. Shape: Generally ovate. Apex is acuminate. The base is rounded. Texture: Smooth. Thickness; Average. Arrangement: Odd pinnate. Venation: Reticulate. Leaf Gloss: Matte finish.

Disease resistance: Average resistance to powdery and downy mildew, black spot, and *Botrytis* under normal growing conditions in Fredensborg, Denmark.

What is claimed is:

1. A new and distinct variety of rose plant of the miniature class named 'Poulpah024', substantially as illustrated and described herein, due to its abundant, red, white, and yellow flowers, vigorous growth, compact habit, suitability for production from softwood cuttings in pots, and durable flowers and foliage that make the variety suitable for distribution in the floral industry.

* * * * *

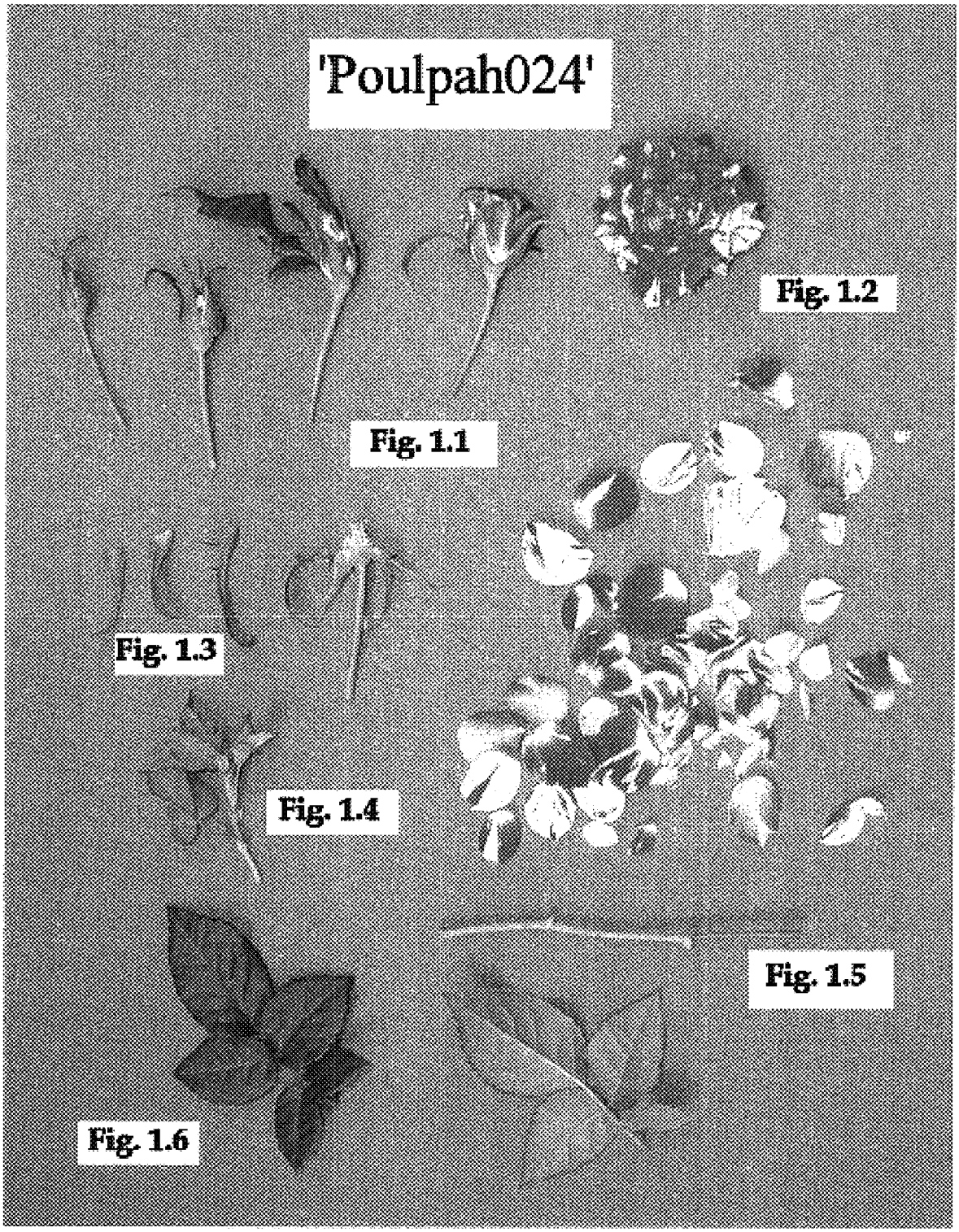
'Poulpah024'
Fig. 1.1
Fig. 1.2
Fig. 1.3
Fig. 1.4
Fig. 1.5
Fig. 1.6